United States Patent
Clementi et al.

(10) Patent No.: US 8,267,909 B2
(45) Date of Patent: Sep. 18, 2012

(54) CANISTER HAVING FLUID FLOW CONTROL

(75) Inventors: Francis J. Clementi, Somerset, PA (US); Joel David Neatrour, Johnstown, PA (US)

(73) Assignee: DeVilbiss Healthcare, LLC, Somerset, PA (US)

( * ) Notice: Subject to any disclaimer, the term of this patent is extended or adjusted under 35 U.S.C. 154(b) by 485 days.

(21) Appl. No.: 12/150,831

(22) Filed: May 1, 2008

(65) Prior Publication Data

US 2009/0275905 A1   Nov. 5, 2009

(51) Int. Cl.
*A61M 1/00* (2006.01)
(52) U.S. Cl. .................. 604/320; 604/319; 604/317
(58) Field of Classification Search .................. 604/319, 604/320, 317
See application file for complete search history.

(56) References Cited

U.S. PATENT DOCUMENTS

| | | | | |
|---|---|---|---|---|
| 3,768,478 A | * | 10/1973 | Fertik et al. ................ | 604/320 |
| 3,963,027 A | | 6/1976 | Muriot | |
| 3,982,538 A | * | 9/1976 | Sharpe ........................ | 604/320 |
| 4,228,798 A | * | 10/1980 | Deaton ........................ | 604/540 |
| 4,275,732 A | * | 6/1981 | Gereg .......................... | 604/320 |
| 4,437,472 A | * | 3/1984 | Naftulin ...................... | 600/580 |
| 4,465,485 A | * | 8/1984 | Kashmer et al. ............. | 604/320 |
| 4,468,226 A | * | 8/1984 | Kurtz et al. .................. | 604/321 |
| 4,487,606 A | * | 12/1984 | Leviton et al. ............... | 604/319 |
| 4,698,060 A | | 10/1987 | D'Antonio et al. | |
| 4,915,691 A | | 4/1990 | Jones et al. | |
| 4,930,997 A | | 6/1990 | Bennett | |
| 5,156,602 A | | 10/1992 | Steffler | |
| 5,185,007 A | * | 2/1993 | Middaugh et al. ........... | 604/320 |
| 5,195,961 A | | 3/1993 | Takahashi et al. | |
| 5,234,419 A | * | 8/1993 | Bryant et al. ................ | 604/320 |
| 5,279,602 A | * | 1/1994 | Middaugh et al. ........... | 604/320 |
| 5,300,050 A | | 4/1994 | Everett, Jr. et al. | |
| 5,466,229 A | | 11/1995 | Elson et al. | |
| 5,589,145 A | | 12/1996 | Kaufman | |
| 5,620,428 A | | 4/1997 | Hand | |
| 5,669,892 A | * | 9/1997 | Keogh et al. ................. | 604/320 |
| 5,807,359 A | | 9/1998 | Bemis et al. | |
| 5,931,822 A | | 8/1999 | Bemis et al. | |
| 6,244,311 B1 | | 6/2001 | Hand et al. | |
| 6,358,218 B1 | | 3/2002 | Want et al. | |
| 6,358,232 B1 | | 3/2002 | Hand et al. | |
| 6,368,310 B1 | | 4/2002 | Bemis et al. | |
| 6,368,311 B1 | | 4/2002 | Valerio et al. | |
| 6,447,473 B1 | | 9/2002 | Levine et al. | |
| 6,494,869 B1 | | 12/2002 | Hand et al. | |

(Continued)

FOREIGN PATENT DOCUMENTS

WO    WO 87/00439    *    1/1987

*Primary Examiner* — Susan Su
(74) *Attorney, Agent, or Firm* — Fox Rothschild, LLP; Dennis M. Carleton

(57) ABSTRACT

A canister for use with a medical suction or aspiration device has a first fluid chamber and a second fluid chamber. The first fluid chamber has an inlet. The second fluid chamber has an outlet port. A splash baffle is disposed between the first fluid chamber and the second fluid chamber. The splash baffle has an aperture formed therethrough to allow for fluid flow from the first fluid chamber to the second fluid chamber. An absorbent valve having voids is disposed within the second fluid chamber and engages a portion of the outlet port. The absorbent valve restricting fluid permeability upon contact with fluid from the first fluid chamber to restrict fluid flow through the outlet port.

13 Claims, 3 Drawing Sheets

U.S. PATENT DOCUMENTS

| | | |
|---|---|---|
| 6,615,826 B1 | 9/2003 | Gabrio et al. |
| 6,648,862 B2 * | 11/2003 | Watson .......................... 604/319 |
| 6,673,055 B2 | 1/2004 | Bemis et al. |
| 6,955,664 B2 | 10/2005 | D'Antonio |
| 7,115,115 B2 | 10/2006 | Bemis et al. |
| 7,153,294 B1 * | 12/2006 | Farrow .......................... 604/319 |
| 7,175,612 B2 | 2/2007 | Felix et al. |
| 2002/0026935 A1 | 3/2002 | Schmidt et al. |
| 2003/0234015 A1 | 12/2003 | Bruce et al. |
| 2007/0163572 A1 | 7/2007 | Addington et al. |

* cited by examiner

CANISTER HAVING FLUID FLOW CONTROL

TECHNICAL FIELD

This invention relates in general to canisters. More specifically, the invention is directed to canisters for use with a medical suction or aspirator device.

BACKGROUND OF THE INVENTION

Medical suction and aspiration devices are used to remove bodily fluids during medical procedures or emergency situations. These suction and aspiration devices often include canisters to receive the bodily fluids. It is desirable to minimize contact between the suctioned fluid within the canister and the device operator. The invention provides a canister having a filtered, shut off device to retain suctioned fluids within the container.

BRIEF SUMMARY OF THE INVENTION

This invention relates to a canister comprising a first fluid chamber having an inlet port and a second fluid chamber having an outlet port. A splash baffle is disposed between the first fluid chamber and the second fluid chamber. The splash baffle has an aperture formed therethrough to allow for fluid flow from the first fluid chamber to the second fluid chamber. An absorbent valve is disposed within the second fluid chamber and further engages the outlet port. The absorbent valve restricts fluid permeability upon contact with fluid from the first fluid chamber to prevent fluid flow through the outlet port.

DESCRIPTION OF THE INVENTION

Figure 1:
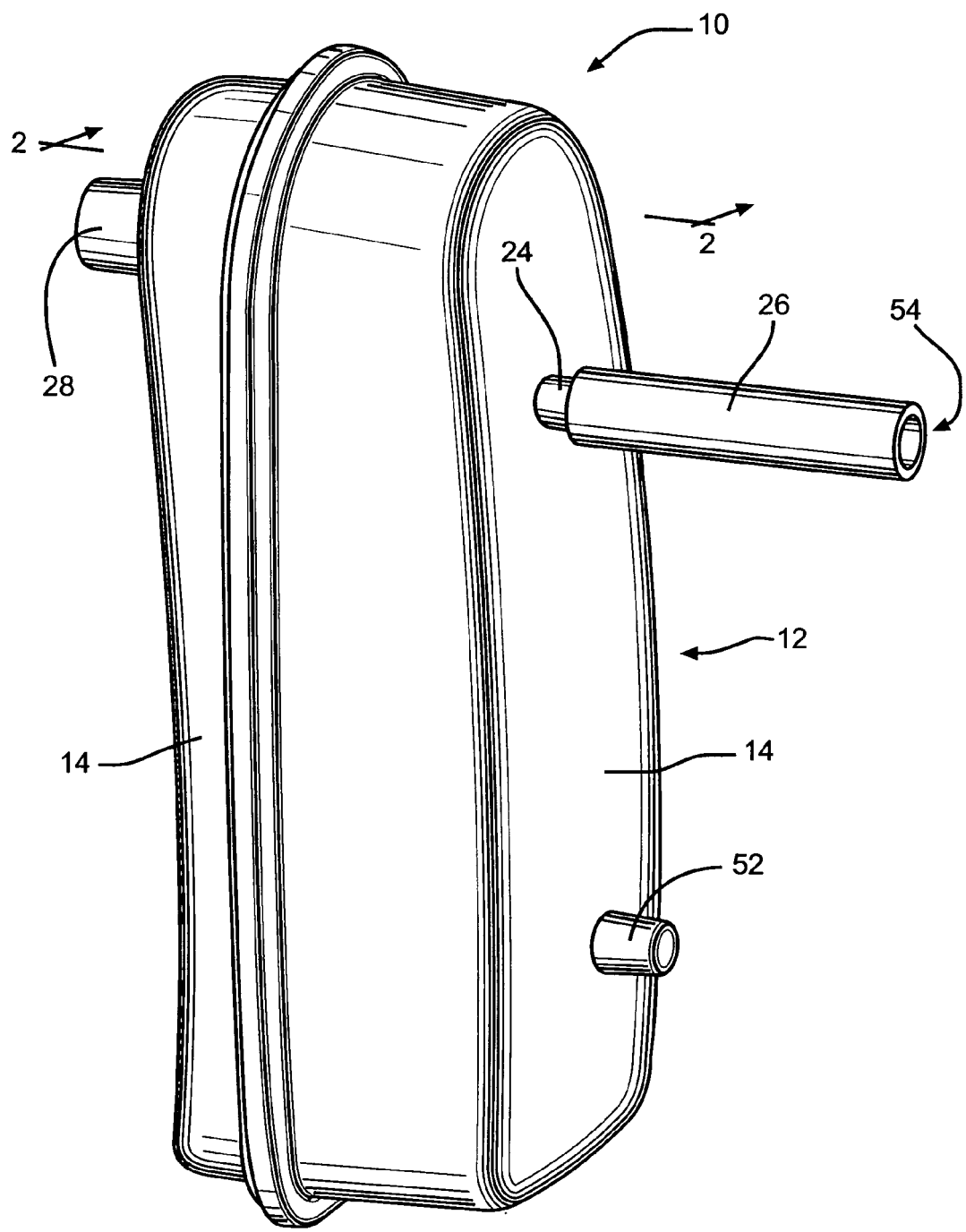
FIG. 1 is a perspective view of a canister according to the invention.
Figure 2:
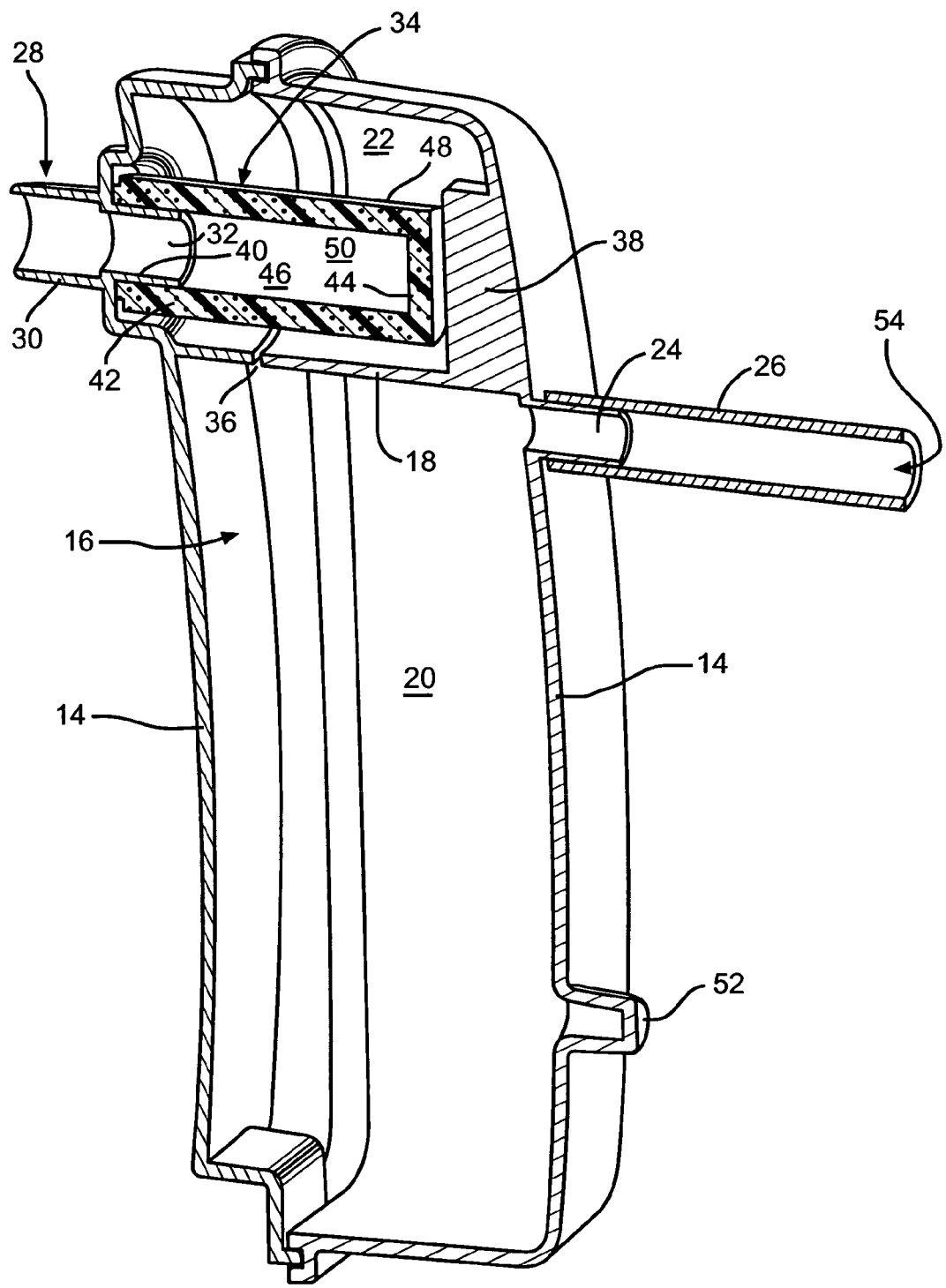
FIG. 2 is a cross-sectional view taken along line 2-2 of FIG. 1.

Referring now to the drawings, a canister according to the invention is indicated by the reference number 10. As shown in FIGS. 1 and 2, the canister 10 has a body portion 12 that includes a perimeter wall 14 defining an interior container cavity 16. The interior container cavity 16 is divided by a splash baffle 18 that defines a first fluid chamber 20 and a second fluid chamber 22. The first fluid chamber 20 is in fluid communication with an inlet port 24 that engages a suction tube 26. The second fluid chamber 22 is in fluid communication with an outlet port 28 having a vacuum source connection 30 and an attachment flange 32. An absorbent valve 34 is disposed within the second fluid chamber 22 and engages the attachment flange 32.

Figure 3:
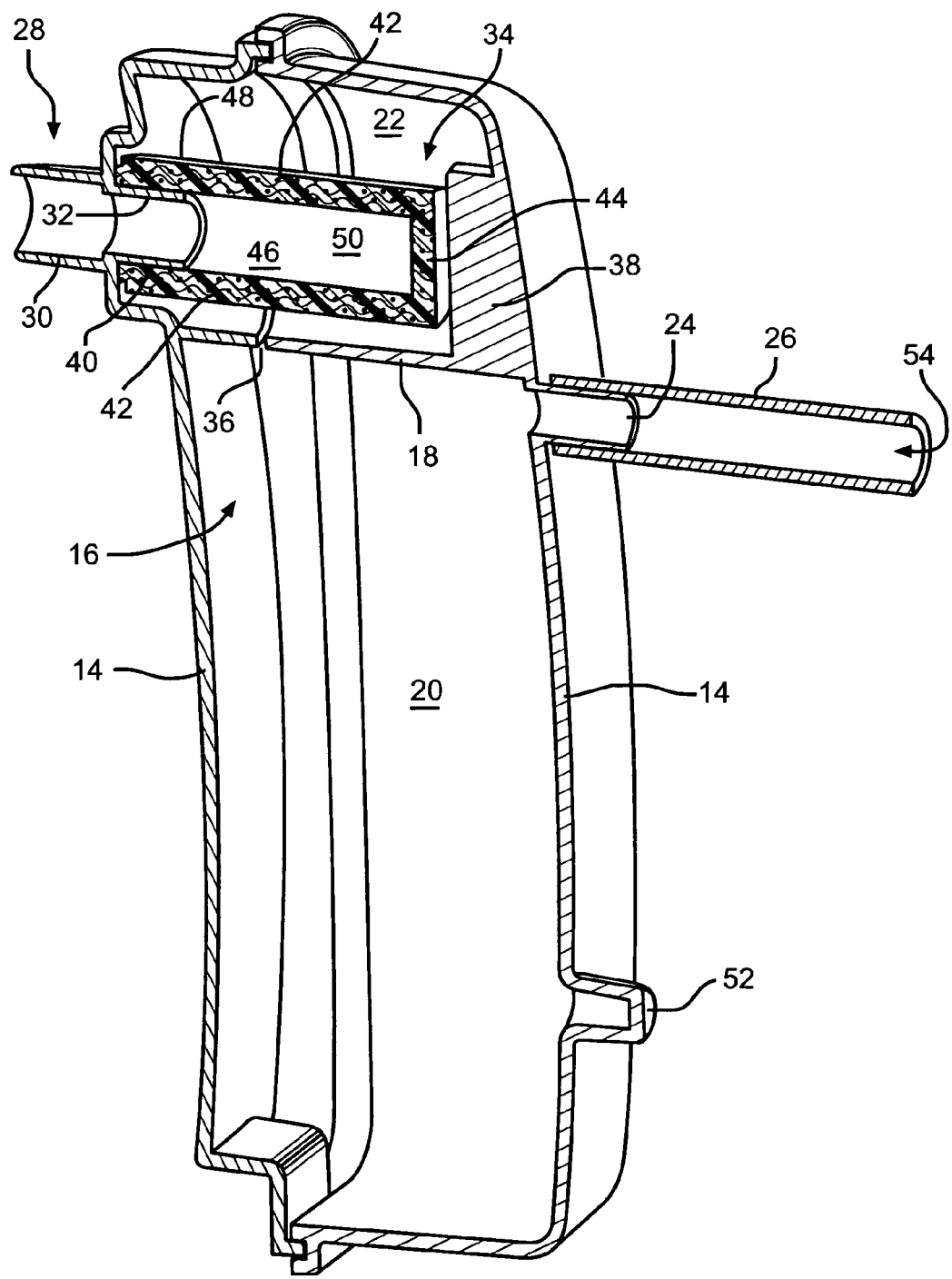
FIG. 3 is a view similar to FIG. 2 showing an expanded absorbent valve.

As shown in FIG. 2, the splash baffle 18 includes an aperture 36 formed therethrough that provides fluid communication between the first and second fluid chambers 20 and 22, and further provides a fluid pathway between the inlet port 24 and the outlet port 28. The aperture 36 restricts fluid contact with the absorbent valve 34 until fluid suctioning requirements cease or the canister 10 is full. The aperture 36 is illustrated in FIGS. 2 and 3 as an elongated slot, however, any suitable opening shape may be used to restrict fluid contact with the absorbent valve 34. The inlet port 24 is illustrated in an adjacent position to the splash baffle 18, though such a position is not required. The inlet port 24 may be positioned on any surface that allows fluid communication between the first fluid chamber 20 and the suction tube 26. The first fluid chamber 20 is illustrated as being larger in volume than the second fluid chamber 22. The volume of the first fluid chamber 20 is constructed to receive and contain the bulk of suctioned material drawn in through the suction tube 26. The volume of the second fluid chamber 22 houses and contains at least a portion of the absorbent valve 34. The second fluid chamber 22 includes a valve seat 38 spaced apart from the attachment flange 32. The valve seat 38 provides a positive positioning of the absorbent valve 34 within the second fluid chamber 22.

The absorbent valve 34 includes an open end 40, a valve wall 42, and a closed end 44. The valve wall 42 and the closed end 44 have an interior surface 46, an exterior surface 48, and cooperate to define an interior space 50. The positive positioning of the valve seat 38 against the closed end 44 ensures that the open end 40 is in sealed engagement with at least a portion of the attachment flange 32. The open end 40 may further be seated against the perimeter wall 14 within the second fluid chamber 22 by the valve seat 38. The valve seat 38 is illustrated as a thin, fin-like structure, though other shapes may be utilized. The shape of the valve seat 38 allows more surface area of the absorbent valve 34 to be exposed when the closed end 44 is seated against the valve seat 38, thus increasing the time between a flow state and a shut off state.

Still referring to FIG. 2, the canister 10 includes a tube stopper 52 extending from the perimeter wall 14. The tube stopper 52 may be positioned at any convenient location on the canister 10. The tube stopper 52 seals or closes off a free end 54 of the suction tube 26 after use and provides an additional way to contain suctioned material within the cavity 16 of the canister 10. The tube stopper 52 is shown as a conical structure projecting from the perimeter wall 14 to engage an inner surface of the suction tube 26. The tube stopper 52 may alternatively project into the cavity 16 and engage an outer surface of the suction tube 26. The canister 10 may be made from a material that is clear, translucent or opaque. The material may be a plastic, such as for example a polystyrene, polyethylene, polypropylene, polyvinyl chloride, polycarbonate, or other suitable materials. The canister 10 may also be of an opaque material and include a translucent section allowing the contents level to be viewed.

As shown in FIGS. 1-3, the canister 10 in operation is connected to a vacuum source, such as a medical suction or aspiration device, (not shown) at the vacuum source connection 30. Negative pressure is applied at the vacuum source connection 30 to evacuate the cavity 16 of the canister 10 and draw fluid, for example bodily fluids such as blood, saliva, vomitus, stomach contents, or other materials, into the suction tube 26. Fluid enters the first fluid cavity 20 from the suction tube 26 and begins to fill the volume therein. As fluid enters the first fluid chamber 20, foaming, splashing, or fluid accumulation causes fluid migration into the second fluid chamber 22. Fluid enters the second fluid chamber 22 through the aperture 36 and contacts the absorbent valve 34.

As fluid contacts the exterior surface 48 of the absorbent valve 34, a fluid absorption characteristic of the material of the absorbent valve 34 reacts with the entering fluid. The material of the absorbent valve 34 may be of a porous structure having interstitial voids, such as between sintered beads or intertwined filaments, thus creating a capillary effect therein. The material of the absorbent valve 34 may also include a reactant medium. FIG. 2 shows the absorbent valve in an open or flow state where the valve wall 42 and closed end 44 allow air to pass from the cavity 16 into the interior space 50 and out the outlet port 28. FIG. 3 shows the absorbent valve 34 in a closed or shut off state wherein fluid flow is restricted from entering the outlet port 28. Upon contact with fluid, the interstitial voids of the material of the valve wall 42 and the closed end 44 gradually reduce to increasingly restrict air and fluid permeability and thus, fluid flow from the second fluid chamber 22. Fluid flow becomes restricted as the incoming fluid or water reacts with the reactant medium and the voids constrict, or clog, through the thickness of the valve wall 42 between the interior surface 46 and the exterior surface 48. Thus, fluid flow slows and eventually ceases to pass into the interior space 50, which is in fluid communication with the outlet port 28.

The absorbent valve 34 is made from a material exhibiting a hydrophilic or hygroscopic property. This fluid absorptive property of the absorbent valve 34 is aided, at least in part, by the capillary action of the interstitial voids of the material. The structure can be made from sintering plastic beads or powders. Such a structure may be formed by a polyethylene plastic having an added cellulose gum filler. Additionally, any suitable plastic or polymer capable of having a porous structure may be a suitable material substitute to support a cellulose gum filler. The cellulose gum filler is used as the reactant medium to reduce the interstitial voids, thus slowing and ceasing fluid flow therethrough.

In operation, the absorbent valve 34 may transition from a flow state to a fluid restricted, shut-off state by a reaction mechanism with the incoming fluid. The porous material of the absorbent valve 34 may include the reactant that becomes solidified or fills the interstitial voids of the valve material. The reactant medium, or the porous material itself, interacts with water or other fluids, either chemically or through the hygroscopic nature of the material, to block fluid flow through the absorbent valve 34. The reaction of the material is such that the porous material may swell upon contact with the suctioned fluid and gradually diminishes the interstitial space of the filamentary structure until the fluid pathways are closed off. The water absorptive nature of the material causes the contraction of the interstitial voids within the absorbent valve 34 at a rate sufficient to prevent suctioned bodily fluids from entering the outlet port 28. Other material state change mechanisms creating a restriction to fluid flow therethrough may be substituted for those described herein without departing from the spirit or scope of the invention.

While the invention has been described with reference to particular embodiments, it should be understood that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiments, but that the invention shall include all embodiments falling within the scope of the claims.

What is claimed is:

1. A canister comprising:
   a perimeter wall defining a first fluid chamber;
   a splash baffle extending horizontally into said first fluid chamber, said splash baffle enclosing a second fluid chamber;
   an inlet port defined in the first fluid chamber;
   an outlet port defined in the second fluid chamber, said outlet port having an attachment flange extending into said second fluid chamber;
   a valve seat disposed in the second fluid chamber opposite said outlet port;
   an elongated slot extending around at least a portion of said splash baffle, said slot being at least partially oriented toward the bottom of said first fluid chamber, said slot allowing fluid flow from the first fluid chamber to the second fluid chamber; and
   a hollow absorbent valve having a closed end and an open end, said open end engaging said attachment flange and said closed end resting on the valve seat, said absorbent valve restricting fluid permeability upon contact with fluid from the first fluid chamber to prevent fluid flow through the outlet port.

2. The canister of claim 1, wherein the inlet port is positioned adjacent to the splash baffle.

3. The canister of claim 1, wherein the first fluid chamber is larger than the second fluid chamber.

4. The canister of claim 1, wherein said valve seat restricts the expansion of said absorbent valve in one direction.

5. The canister of claim 1, wherein the outlet port includes a vacuum source connection extending outwardly from the exterior of said perimeter wall.

6. The canister of claim 1, wherein the splash baffle restricts splashing fluid from the first fluid chamber from entering the second fluid chamber.

7. The canister of claim 1, wherein the absorbent valve has a fluid absorption characteristic.

8. The canister of claim 7, wherein the absorbent valve becomes fluid restrictive in response to the fluid absorption characteristic when in contact with fluid flow from the first fluid chamber.

9. The canister of claim 7, wherein the fluid absorption characteristic is hydrophilic.

10. The canister of claim 7, wherein the fluid absorption characteristic is hygroscopic.

11. The canister of claim 1, wherein the absorbent valve is made from a polymer material.

12. The canister of claim 11 wherein the polymer material is polyethylene plastic.

13. The canister of claim 12, wherein the polymer material includes a cellulose gum filler.

* * * * *